(12) United States Patent  (10) Patent No.: US 7,578,807 B2
Wyss et al.  (45) Date of Patent: Aug. 25, 2009

(54) INSERTION AID FOR INSERTING A CANNULA OF A CATHETER HEAD INTO ORGANIC TISSUE

(75) Inventors: Martin Wyss, Konolfingen (CH); Ronny-Patrick Horisberger, Burgdorf (CH)

(73) Assignee: Disetronic Licensing AG, Burgdorf (CH)

( * ) Notice: Subject to any disclaimer, the term of this patent is extended or adjusted under 35 U.S.C. 154(b) by 672 days.

(21) Appl. No.: 11/130,816

(22) Filed: May 17, 2005

(65) Prior Publication Data
US 2005/0251098 A1 Nov. 10, 2005

Related U.S. Application Data

(63) Continuation of application No. PCT/EP2003/011730, filed on Oct. 23, 2003.

(30) Foreign Application Priority Data
Nov. 21, 2002 (DE) ................. 102 54 443

(51) Int. Cl.
*A61M 5/00* (2006.01)
(52) U.S. Cl. .................................... 604/263
(58) Field of Classification Search ............ 604/263, 604/110, 164.08, 264, 192, 177, 174, 162, 604/164.04
See application file for complete search history.

(56) References Cited

U.S. PATENT DOCUMENTS

| 4,664,259 | A | | 5/1987 | Landis |
| 4,909,792 | A | | 3/1990 | Norelli |
| 5,147,319 | A | * | 9/1992 | Ishikawa et al. ............ 604/174 |
| 6,156,012 | A | * | 12/2000 | Nathan ........................ 604/192 |
| 6,413,243 | B1 | * | 7/2002 | Geist ........................... 604/192 |
| 6,500,155 | B2 | * | 12/2002 | Sasso .......................... 604/177 |
| 6,911,020 | B2 | * | 6/2005 | Raines ......................... 604/177 |

FOREIGN PATENT DOCUMENTS

| DE | 694 22 073 T2 | 4/2000 |
| FR | 2 725 902 | 4/1996 |
| WO | WO 00/03757 | 1/2000 |

* cited by examiner

*Primary Examiner*—Kevin C Sirmons
*Assistant Examiner*—Catherine N Witczak
(74) *Attorney, Agent, or Firm*—Dorsey & Whitney LLP

(57) ABSTRACT

An insertion aid for inserting a cannula of a catheter head into organic tissue, in particular a catheter head for administering a liquid active substance, wherein the insertion aid includes a guide needle that is fixed to a grip section for removably inserting and stabilising the cannula during insertion into the organic tissue and a needle shield, having at least two sections, which is secured in a pivotable manner to the grip section and which encases and shields the guide needle when the insertion aid is separated from the catheter head.

5 Claims, 4 Drawing Sheets

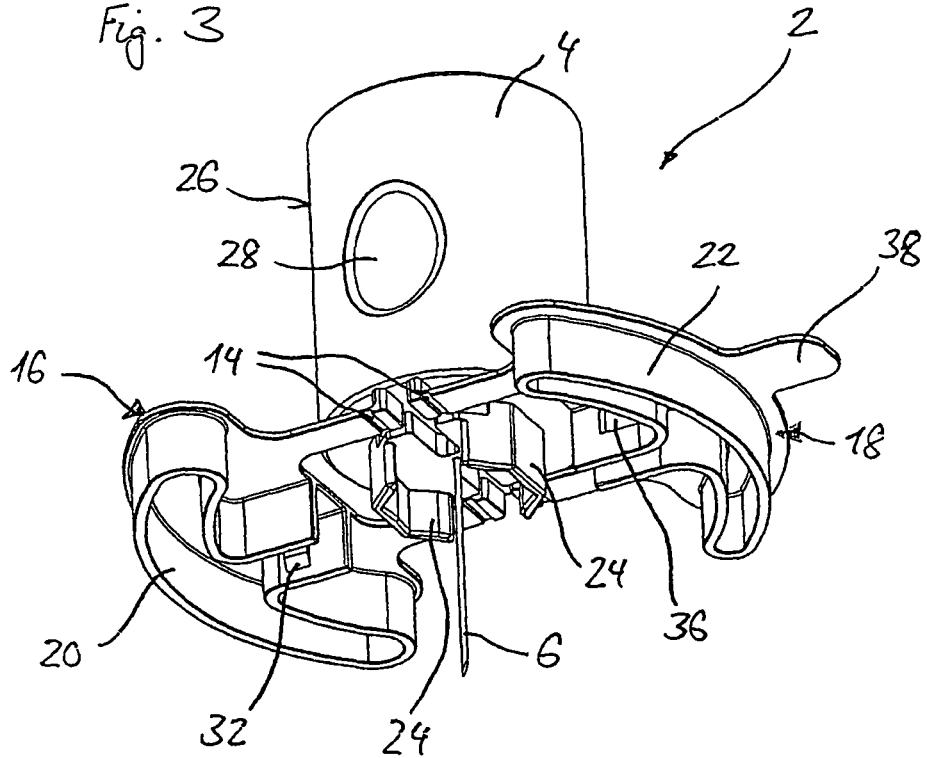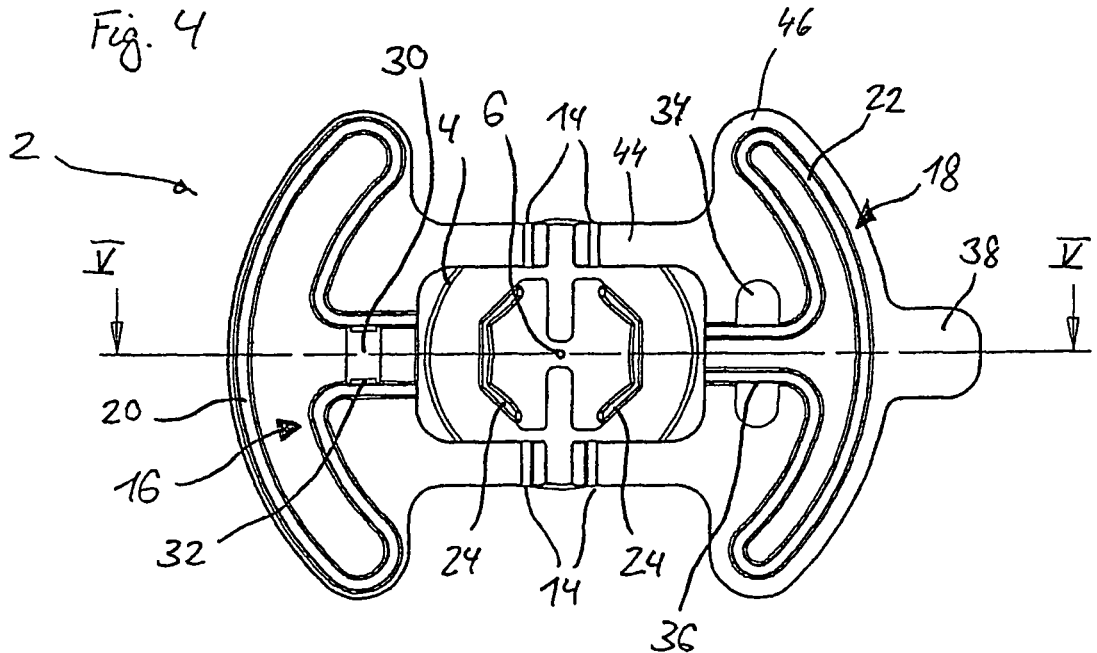

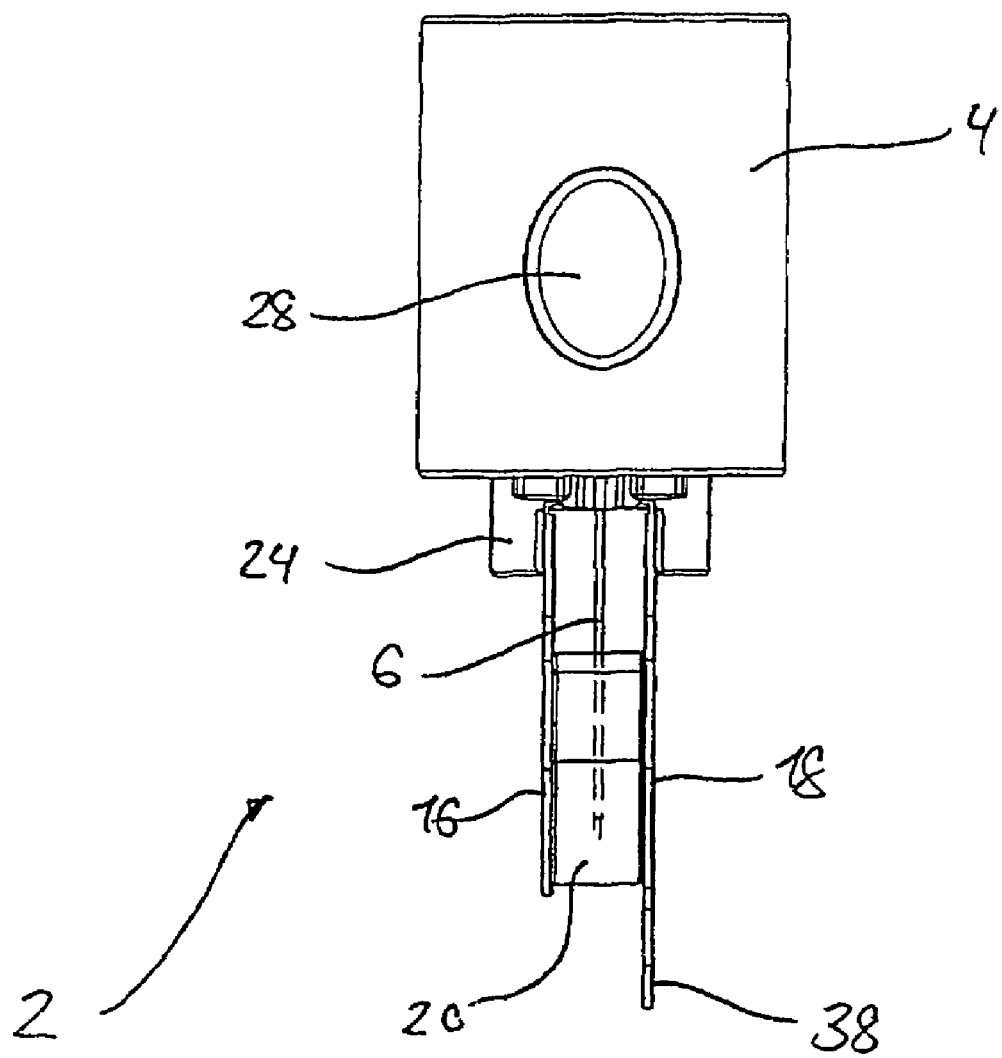

INSERTION AID FOR INSERTING A CANNULA OF A CATHETER HEAD INTO ORGANIC TISSUE

CROSS-REFERENCE TO RELATED APPLICATION(S)

This application is a continuation of International Patent Application No. PCT/EP2003/011730, filed on Oct. 23, 2003, which claims priority to German Application No. 102 54 443.3, filed on Nov. 21, 2002, the contents of which are incorporated herein by reference in their entirety.

BACKGROUND

The present invention relates to devices and methods for using cannulae and the like and, more particularly, to an insertion aid for inserting a cannula of a catheter head into organic tissue, in particular a catheter head for administering a liquid active substance.

Such catheter heads are used in conjunction with infusion devices, for example, so that a patient to whom a fluid is to be administered continuously or repeatedly does not need to have his or her skin repeatedly punctured. Part of the catheter head remains on the patient, namely a cannula housing together with the cannula protruding from it. Another part of the catheter head, having a connection element with a fluid conduit, can be detached from and reconnected to the cannula housing. By means of the connection element, an injection device or an infusion device can be repeatedly attached to the cannula housing and removed from it again, for example in order to exchange a container of fluid or to perform other maneuvers on the injection device or the infusion device. Such a catheter head can also be used, for example, to withdraw analysis fluid from a patient's body or to pass the analysis fluid into and back out of the body. The catheter head usually has a soft cannula which extends into the tissue and which in most cases cannot be introduced into the body without a stabilizing insertion aid. In particular, a soft cannula has to be guided and stabilized in order to puncture the outer layers of skin.

To guide and stabilize the soft cannula of the catheter head, an insertion aid is known which has a guide needle to be pushed into the soft cannula and which can be removed and disposed of after the catheter head is anchored in or on the body or the organic tissue. To exclude any risk of injury to the person handling the insertion aid when removing and disposing of it, it is expedient to provide the guide needle with a needle guard which can largely prevent direct contact and risk of injury. A device for inserting a catheter head with the aid of a stiffening guide needle is known from WO 00/03757. This device has a guide needle which is anchored on a grip section and which, after removal from the catheter head, can be covered with the aid of a protective device. For this purpose, a shield with a contour in the shape of a segment of a cylinder is folded partially about the needle and is locked in position with the aid of interlocking hooks. The guide needle is thus provided with a protective and shielding enclosure, with the result that the device can be disposed of easily and without danger.

SUMMARY

An object of the present invention is to make available an insertion aid for inserting a cannula of a catheter head into organic tissue, which permits safe handling of a needle guard and can reliably prevent contact with the guide needle after removal from the catheter head.

According to the invention, an insertion aid of the type described at the outset is provided with a needle guard, comprising at least two parts, which is anchored in a pivotable manner on a grip section and which encloses and shields the guide needle when the insertion aid is separated from the catheter head. In some embodiments, the two parts of the needle guard are preferably pivotable with respect to the grip section, whereby they are moveable toward each other and can be locked together. The insertion aid is needed to assist in puncturing the skin when using infusion sets with a soft cannula. After use, the insertion or puncture aid is separated from the infusion set and can be disposed of. To ensure that the user or a third party cannot be injured by the needle, the latter is covered immediately after removal from the infusion set. The present invention affords a simple and safe way of guaranteeing this protection. In particular, the pivotable parts of the needle guard mean that recapping is unnecessary. The movement of the fingers during use of the needle guard is advantageously not directed toward the needle tip, but instead laterally with respect to the latter and obliquely away from it. The interlocking of the two parts of the needle guard ensures that, during or after its disposal, the needle cannot be inadvertently exposed and thus cause accidental contact. The interlocking can be cancelled out preferably only by applying a certain tensile force, for example if the insertion aid is to be recycled.

In one embodiment, the present invention comprises an insertion aid comprising a needle guard comprising a grip section and at least two parts moveably coupled to the grip section, said two parts being moveable relative to the grip section to substantially enclose a guide needle after a use of the guide needle.

In a preferred illustrative embodiment, the two parts of the needle guard are anchored, connected or coupled in a pivotable and/or foldable manner on the grip section via, in each case, at least one film or living hinge. The hinges preferably have an easy locking action in one position in which the parts of the insertion aid designed as flat shields are generally co-planar and perpendicular to the shaft and tip of the needle. This defined locking position can be overcome by turning or moving the shields inwardly, ie., moving their respective free edges toward each other, with application of minimal force so that, after the locking position has been overcome, the two parts can easily move toward one another, after which the two parts of the needle guard can be interlocked in their end position in which they are generally parallel.

In some embodiments, the two parts of the needle guard are preferably each designed as disk-shaped shields. In a further embodiment of the invention, the shields each have arc-shaped web sections which, when they are locked together, slide one inside the other and form a labyrinthine enclosure and shielding for the guide needle. The web sections slide in one another in such a way that a substantially tight and, at the same time, stabilizing connection of the shields is possible.

In some embodiments, a centering web spaced apart from the guide needle is preferably arranged on a lower end face of the grip section, the centering web being able to ensure correct centering and positioning of the insertion aid on the catheter head. The shields of the needle guard are configured in such a way that this centering web is not in the way when the shields are folded closed and locked together. This can be made possible by suitably configuring the hinges in two parts.

In some embodiments, the grip section preferably has a cylindrical contour with grip surfaces lying opposite one another on its outer circumferential surface. In this way, the insertion aid can be easily and safely handled so that, when the two parts of the needle guard engage one inside the other, the grip section is at the same time held secure. The grip section and the needle guard are preferably in one piece and can be made, for example, of plastic which can be processed in, for example, an injection molding process. In this way, the hinges can be produced, and the guide needles can be secured in the grip section, in one operation.

When the parts of the needle guard are locked together, the guide needle is substantially enclosed by these parts, in some preferred embodiments without touching them, and it is in this way safely protected from touching during disposal of the insertion aid.

BRIEF DESCRIPTION OF THE DRAWINGS

FIG. 3 shows the insertion aid according to FIG. 2 in an oblique view from underneath, FIG. 4 is a bottom view of the insertion aid according to FIGS. 1 through 3, FIG. 7 is a side view of the insertion aid with the parts of the needle guard locked together as in FIG. 6.

DETAILED DESCRIPTION

Figure 1:
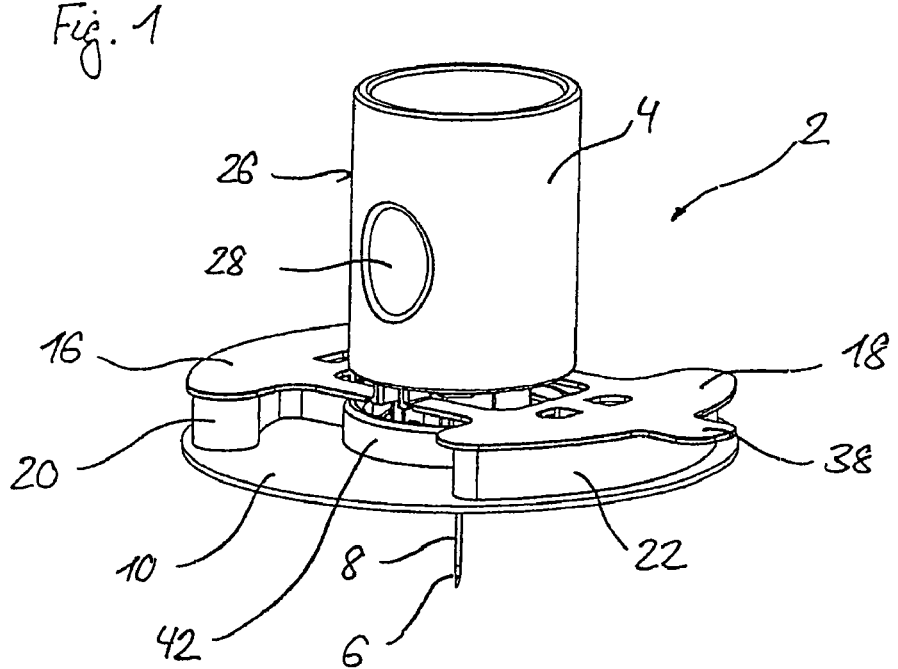
FIG. 1 is a schematic perspective view of an insertion aid, according to the present invention, fitted on a catheter head.
Figure 2:
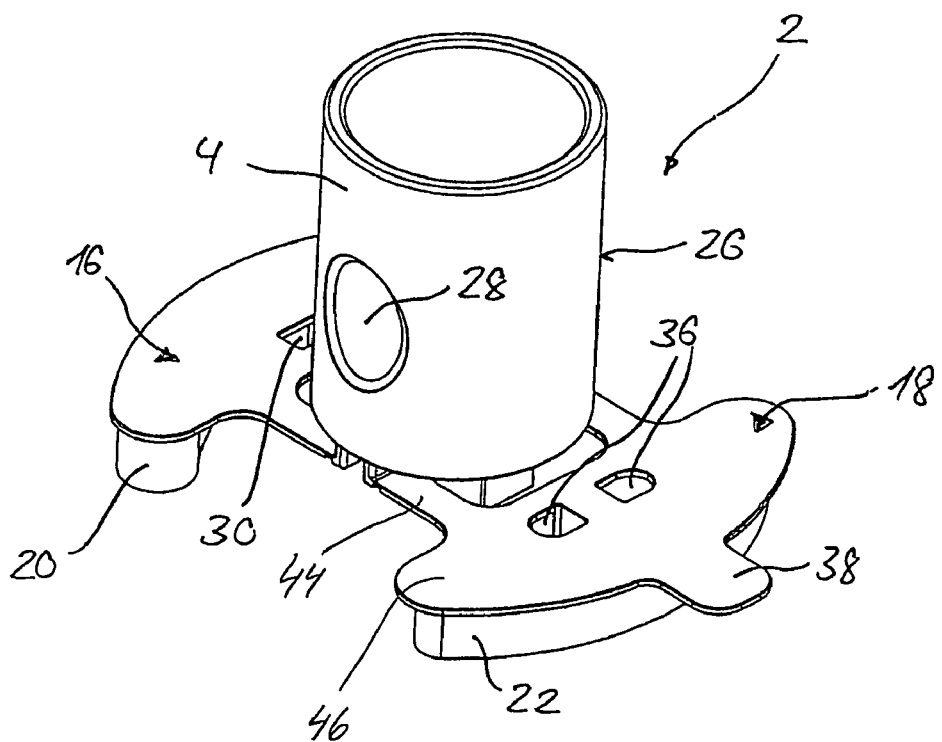
FIG. 2 is a schematic perspective view of the insertion aid according to FIG. 1 released from the catheter head.

FIGS. 1 through 3 depict an insertion aid 2 according to the present invention in a perspective schematic view. The insertion aid 2 comprises a cylindrical grip section 4 and, anchored on this, a guide needle 6 for stabilizing and guiding a soft cannula 8 of a catheter head of which, in the view shown in FIG. 1, only a plaster 10 and a guide section 42 can be seen. When the catheter head is in the applied position, the plaster 10 lies on the skin of the organic tissue. The cannula 8 is intended to puncture the skin and permit delivery and/or removal of fluid into and out of the organic tissue. After removal of the insertion aid 2, an infusion set or the like can be placed on the guide section 42 and anchored there.

The guide needle 6 has an external diameter which substantially corresponds to an internal diameter of the soft cannula 8. By means of the stiffening and stabilizing of the cannula 8 and a beveled tip of the guide needle 6, this can easily penetrate the tissue and be applied at the intended infusion site.

Figure 6:
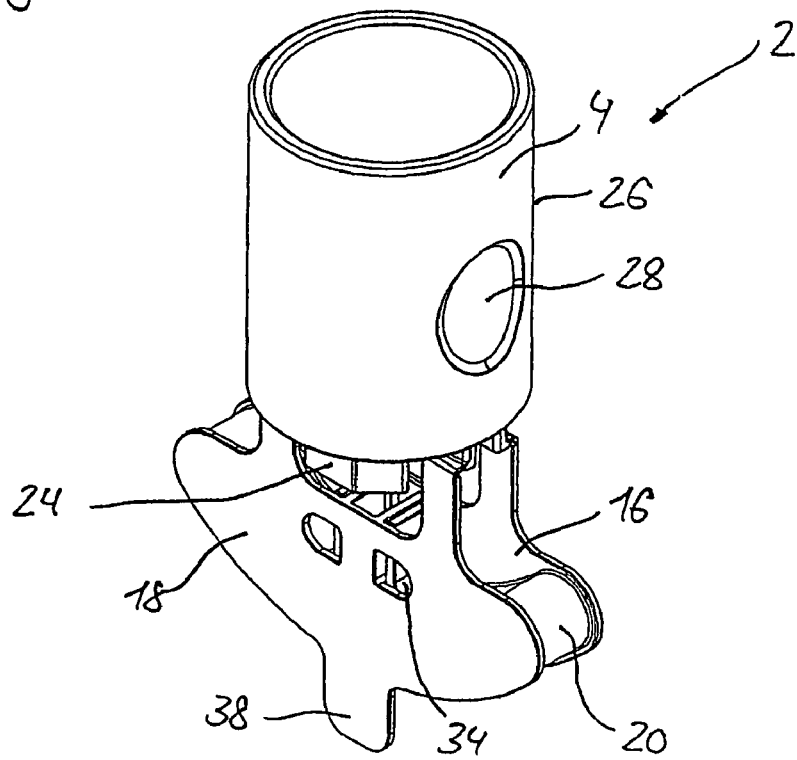
FIG. 6 shows the insertion aid according to the present invention with the parts of a needle guard locked together.

The grip section 4 has a cylindrical outer circumferential surface 26 with two grip surfaces 28 lying opposite one another and intended for gripping with two fingers. On the lower end face of the grip section 4 from which the guide needle 6 also protrudes, first and second shields 16, 18 are secured in a pivotable manner via film or living hinges 14. Other suitable hinge forms or connectors which enable a relative folding movement may be used. When the insertion aid 2 is removed, the shields can be pivoted over the guide needle 6 and can shield the latter from contact from outside. The first and second shields 16, 18 each have a disk-shaped contour, with a tab 38 formed on the second shield 18. The tab 38 indicates to the user, among other things, in which orientation the connection element is connected to the cannula housing of the catheter head. When the two shields 16, 18 are joined and locked together, the tab 38 points vertically downward (cf. FIGS. 6 and 7).

In a plan view, the shields 16 and 18 each have an approximately mushroom-shaped silhouette, with a narrower section 44 being anchored at one end on the grip section 4 via the hinges 14. At its opposite end, the narrower section 44 is adjoined by a roof-like wider section 46 which has a straight main face pointing toward the narrow section 44, and, lying away from this, a curved face. At the sides, the straight main face merges into the curved face via a radius of curvature. The curved faces of the wide section 46 each point downward when the two parts are locked together. The grip tab 38 points vertically downward (cf. FIGS. 6 and 7) from the curved face of the second shield 18. The narrow sections 44 have a width which approximately corresponds to the diameter of the outer circumferential surface 26 of the grip section 4. The wide sections 46 are approximately double or slightly less than double the width of the narrow sections 44.

On the undersides of the first and second shields 16, 18 facing away from the grip section 4 when the needle guard 12 is in the folded-out state, there are in each case web sections 20, 22 which follow the arc of the outer edge contours of the wide sections 46 of the shields 16, 18 and which, through engagement and interlocking of the two shields, permit a labyrinthine enclosure. The first web section 20 has a slightly larger contour engaging round the second web section 22, with the result that the second web section 22 is completely enclosed by the first web section 20 when the shields are engaged in one another (cf. FIGS. 6 and 7). The second web section 22 of the second shield 18 does not, however, follow the contour of the grip tab 38, but instead only the contours of the wide section 46. On the sides of the narrower section 44 facing toward the grip section 4, the web sections 20, 22 are in each case open, so that they do not collide with the guide needle 6. The web sections 20, 22 thus do not follow the narrow section 44, but instead end at this. Thus, the web sections 20, 22 in each case as a whole have a mushroom-like profile which follows an area of the outer contour of the shields 16, 18. The contour and profile of the web sections 20, 22 can be seen in FIGS. 3 and 4.

Provided around the guide needle 6, and spaced apart from it, there is a centering web 24 which comprises two webs in the shape of generally semicircular segments and which is used to ensure correct and accurate placement of the insertion aid 2 on the catheter head (not shown). This centering web 24 is likewise illustrated in FIGS. 3 and 4.

To ensure that the shields 16, 18 do not collide with the centering web 24 when folded together, their film hinges 14 are in two parts and are arranged on both sides of the centering web 24, i.e., at the edges of the lower end face of the grip section 4. The two short film hinges of each of the two shields 16, 18 are continued in each case by a narrow connecting section. The two connecting sections of each shield 16, 18 thus form the narrow sections 44 thereof and each open into the wider section 46.

The shields have corresponding catch connections, a recess on the first shield 16 being provided with catches 32 arranged on the first web section 20. On the second shield 18, at its second web section 22, there are corresponding undercuts 36 into which the catches 32 each engage and thus ensure locking of the two parts. The two undercuts 36 in the second web section 22 of the second shield 18 adjoin two recesses 34 in the flat upper face of the shield. The catches 32 adjoin a first recess 30 on the upper face of the first shield 16.

Figure 5:
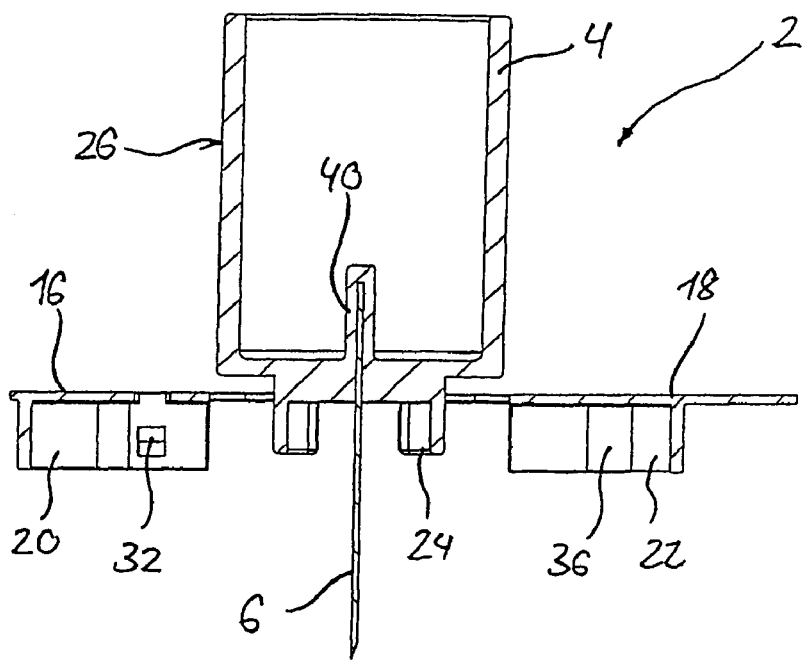
FIG. 5 is a longitudinal section through the insertion aid according to the invention along section line V-V in FIG. 4.

As is illustrated in FIG. 5, the guide needle 6 is secured with its upper section in an anchor 40 in the grip section 4. In a preferred embodiment, the grip section 4, and the shields 16, 18 anchored thereon via the hinges 14, can be made of plastic in an injection molding process. The guide needle 6 can in this way be easily secured in the grip section 4 or in its anchor 40 during the injection molding process. The hinges 14 too can be produced by an injection molding process, with the result that they can be produced along with the other components in a joint operation.

The two shields 16, 18 can be moved toward one another and pivoted relative to one another, via the hinges 14 at the lower end face of the grip section 4, until the catches 32 lock in the undercuts 36. The second web section 22 is at the same time substantially completely enclosed by the first web section 20 (cf. FIG. 6). As is illustrated in FIG. 7, the guide needle 6 in this case is suitably completely shielded and enclosed by the two shields 16, 18 and by the web sections 20, 22 engaged in one another. In this way, when the insertion aid 2 is removed from the catheter head and disposed of, there is no risk of injury posed by the guide needle 6.

While various embodiments, including preferred embodiments, of the present invention have been described herein, it is contemplated that various modifications could be made without deviating from the spirit of the present invention. Accordingly, it is intended that the scope of the present invention be dictated by the appended claims.

The invention claimed is:

1. An insertion aid for inserting a cannula of a catheter head into organic tissue comprising:
    a guide needle fixed to a grip section for removable introduction and stabilizing of the cannula during insertion into the organic tissue;
    a centering web extending from a lower end face of the grip section provided around and spaced apart from the guide needle and configured for facilitating placement of the insertion aid on the catheter head;
    a needle guard, comprising two disc-shaped shields anchored in a pivotable manner on opposite sides of the lower end face of the grip section, each of the shields comprising a narrower section anchored at one end to the lower end face of the grip section via a pair of hinges, and at the other end is adjoined by a roof-like wider section, wherein the two disc-shaped shields of the needle guard can be pivoted from a first position oriented substantially perpendicular to the longitudinal direction of the guide needle, for insertion of the guide needle into the cannula, to a second position oriented substantially parallel to the longitudinal direction of the guide needle, for locking the disc-shaped shields together in the second position; and
    a web section extending from an underside of each of the disc-shaped shield in a direction parallel to the guide needle when the shields are in the first position, wherein a first web section comprises a profile that follows the contours of the roof-like wider section of its respective shield, and wherein a second web section comprises a profile that follows the contours of the roof-like wider section of its respective shield and is slightly larger that the first web section such that, when the shields are in the second position, the second web section encloses the first web section.

2. The insertion aid as claimed in claim 1, wherein one of said web sections comprises a catch and the other of said web sections comprises at least one undercut such that when the shields are in the second position, the catch and the undercut engage and the web sections can be locked together.

3. The insertion aid as claimed in claim 1, wherein the pair of hinges coupling each shield to the lower end face of the grip section comprise film hinges.

4. The insertion aid as claimed in claim 1, wherein the grip section has a cylindrical contour with grip surfaces lying opposite one another on its outer circumferential surface.

5. The insertion aid as claimed in claim 1, wherein the grip section and the needle guard are in configured as one piece and are made of plastic.

* * * * *